(12) United States Patent
Mase et al.

(10) Patent No.: US 11,237,148 B2
(45) Date of Patent: ***Feb. 1, 2022

(54) FLOOD DISASTER PREDICTION

(71) Applicant: NEC Corporation, Tokyo (JP)

(72) Inventors: Ryota Mase, Tokyo (JP); Katsuhiro Ochiai, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/919,579

(22) Filed: Jul. 2, 2020

(65) Prior Publication Data

US 2020/0333315 A1   Oct. 22, 2020

Related U.S. Application Data

(63) Continuation of application No. 16/417,890, filed on May 21, 2019, now Pat. No. 10,761,076, which is a (Continued)

(30) Foreign Application Priority Data

Sep. 14, 2015   (JP) ................................. 2015-180291

(51) Int. Cl.
*G01N 33/24* (2006.01)
*G08B 21/20* (2006.01)

(52) U.S. Cl.
CPC .......... *G01N 33/246* (2013.01); *G01N 33/24* (2013.01); *G08B 21/20* (2013.01)

(58) Field of Classification Search
CPC ...... G01N 22/04; G01N 27/22; G01N 27/223; G01N 33/24; G01N 33/243; G01N 33/246;
(Continued)

(56) References Cited

U.S. PATENT DOCUMENTS 7,136,756 B1   11/2006   Vieux et al.
8,606,520 B2   12/2013   Hong ..................... G01N 21/55
                                                                  356/627
(Continued)

FOREIGN PATENT DOCUMENTS

JP   2005-200972 A   7/2005
JP   2007-11582 A   1/2007
(Continued)

OTHER PUBLICATIONS

Tanaka et al., "Flood Warning/Advisory Improvement based on JMA Runoff Index". Weather Service Bulletin, vol. 75, No. 2, 2008. pp. 35-69.

(Continued)

*Primary Examiner* — Van T Trieu

(57) ABSTRACT

Moisture content information in soil at a specified site is acquired. Moisture content information a ground surface within a given range that includes the specified site is acquired. An amount of runoff or storage volume of water on the ground surface or in a ground at a freely-selected site in the given range is calculated based on the moisture content information in soil and the moisture content information at the ground. A degree of risk of flood disaster at the freely-selected site within the given range is calculated based on the amount of runoff or storage volume of water on the ground surface. A point where there is the risk of flood disaster within the given range is determined and highlighted based on the degree of risk of flood disaster.

6 Claims, 8 Drawing Sheets

Related U.S. Application Data continuation of application No. 15/755,620, filed as application No. PCT/JP2016/004127 on Sep. 12, 2016, now Pat. No. 10,330,661.

(58) Field of Classification Search
CPC .. G01W 1/02; G01W 2001/006; G08B 21/18; G08B 21/182; G08B 21/20; G06Q 10/04; G06Q 50/26
See application file for complete search history.

(56) References Cited

U.S. PATENT DOCUMENTS

| | | | |
|---|---|---|---|
| 2008/0004809 A1* | 1/2008 | Tritico | E02D 3/02 702/2 |
| 2012/0078515 A1 | 3/2012 | Tritico | E02D 3/02 702/2 |
| 2012/0206258 A1 | 8/2012 | Ramesh | G02B 21/10 340/539.22 |
| 2013/0132045 A1 | 5/2013 | Mello et al. | |
| 2014/0159915 A1 | 6/2014 | Hong | H04Q 9/00 |
| 2014/0343855 A1 | 11/2014 | AghaKouchak | G01W 1/10 702/3 |
| 2017/0268874 A1 | 9/2017 | Kasahara | G01C 9/02 |

FOREIGN PATENT DOCUMENTS

| | | |
|---|---|---|
| JP | 2008-050903 A | 3/2008 |
| JP | 2014-123236 A | 7/2014 |
| JP | 5537883 B2 | 7/2014 |
| JP | 2015-129689 A | 7/2015 |

OTHER PUBLICATIONS

Aida et al., "Study on Development of a Frequently Applicable SAR Algorithm for Soil Moisture Using ALOS/PALSAR", Proceecings of the Japanese Conference on Hydraulics, vol. 70, No. 4, 2014, pp. I_589-I_594.

Kasahara et al., "Study of the Slope Stability Analysis Technique using Real-time Measuring Sensor (1)", Proceedings of the 2015 IEICE General Conference, 2015, p. 262 (A-18-4).

Ishihara et al., "Runoff Model for Flood Forecasting", Bulletin of the Disaster Prevention Research Institute, vol. 29, Part 1, No. 260, Jul. 1979, pp. 27-43 (18 pages total).

Okada, "Soil Moisture Index", the Japanese Geotechnical Society, vol. 57, No. 8 (619). Aug. 2009. pp. 56-57.

Toyoda, "Development of Meteorological Prediction Model and Estimation of Soil Water Index or Reducing Sediment Disaster", the Japanese Geotechnical Society, vol. 61, No. 11/12, Nov./Dec. 2013, pp. 10-13.

Makihara et al., "A Verification of the Performance of a Tark Model for Slope Failure Prediction", Journal of Meteorological Research, vol. 45, No. 2, 1993, pp. 35-70.

English Translation of International Search Report dated Dec. 6, 2016 Issued by the International Searching Authority in corresponding application No. PCT/JP2016/004127.

Japanese Office Action for JP Application No. 2017-540494 dated May 28, 2020 with English Translation.

Japanese Office Communication for JP Application No. 2020-144127 dated Aug. 31, 2021 with English Translation.

* cited by examiner

FLOOD DISASTER PREDICTION

The present application is a Continuation application of Ser. No. 16/417,890 filed on May 21, 2019, which issued as U.S. Pat. No. 10,761,976 on Sep. 1, 2020 and is a Continuation application of Ser. No. 15/755,620 filed on Feb. 27, 2018, which issued as U.S. Pat. No. 10,330,661 on Jun. 25, 2019, which is a National Stage Entry of PCT/JP2016/004127 filed on Sep. 12, 2016, which claims priority from Japanese Patent Application 2015-180291 filed on Sep. 14, 2015, the contents of all of which are incorporated herein by reference, in their entirety.

TECHNICAL FIELD

The present invention relates to a system, a device, a method, and a program recording medium that predict an occurrence of a disaster caused by rainfall, such as a landslide disaster and a flood disaster.

BACKGROUND ART

In order to cope with scale expansion or frequency increase of landslide disasters or flood disasters due to frequent occurrence of abnormal weather in recent years, issuance of heavy rainfall and flood warning or advisory, prediction of risk of a landslide, and the like are conducted by the Meteorological Agency, using a soil water index and a basin water index, which are considered to be good indices for such disasters.

The soil water index is an index into which quantity indicating how much fallen rain has been retained inside soil (hereinafter, simply referred to as "in soil") is transformed based on rainfall amount data, using a tank model. In the above, the tank model models a process in which fallen rain flows on a surface of the ground into a river or seeps into the ground by likening the process of tanks having some outlets, as illustrated in FIG. 1.

When using the tank model, in general, a surface of the ground is divided into 5 km square lattice (mesh) elements and calculation is performed for each lattice element using tanks stacked in three stages. On a side face of each of the tanks stacked in three stages, a runoff outlet which represents that water runs off to the surrounding soil is formed, and on the bottom face thereof, a seepage runoff outlet which represents that water seeps into a deeper portion is formed. Runoff volume from the runoff outlet on the side face of the first tank corresponds to surface runoff, runoff volume from the runoff outlet on the side face of the second tank corresponds to seepage runoff at a surface layer, and runoff volume from the runoff outlet on the side face of the third tank corresponds to runoff as groundwater. In addition, inflow to the first tank corresponds to precipitation, inflow to the second tank corresponds to runoff from the seepage runoff outlet of the first tank, and inflow to the third tank corresponds to runoff from the seepage runoff outlet of the second tank. The soil water index represents the total moisture content (the amount of storage) remaining in the respective tanks and corresponds to moisture content in soil.

A landslide disaster such as a debris flow and a landslide caused by heavy rain has a higher occurrence probability as moisture content in soil increases, and there is a case where rain that fell many days earlier may influence an occurrence of a landslide disaster. The soil water index is used for a criterion for issuance of landslide alert information and heavy rain warning or advisory, which meteorological observatories in various regions issue, as an index representing increase in risk of occurrence of a landslide disaster because of heavy rain.

PTL 1 discloses a disaster prediction system and a disaster prediction method using the soil water index. The system disclosed in PTL 1 sets an inclination direction and an inclination angle based on terrain data for each preset fixed section, and determines a surface runoff coefficient that is a coefficient relating to surface runoff of water on the ground surface and a soil runoff coefficient that is a coefficient relating to seepage runoff in the ground, based on the inclination direction and the inclination angle. The system calculates a degree of risk for each section at every unit time based on the soil water index, the surface runoff coefficient, and the soil runoff coefficient for each section, and displays the degree of risk in the section.

NPL 1 describes a calculation method of a basin water index. The basin water index is an index how much degree rainwater having fallen in the basin of a river influences downstream areas, obtained based on the amount of rain fallen in the past (radar-raingauge analyzed precipitation) and the amount of rain forecast to fall within several hours thereafter (short-term precipitation forecast), by calculating of a runoff process and a flow down process. In the method described in NPL 1, a surface of the ground is partitioned into 5 km square sections in a runoff process, and a process in which rain having fallen in each section runs off to a river is calculated using a tank model.

The method described in NPL 1 takes a fact into consideration that most fallen rain flows on the surface of the ground in an urban area in which the ground surface is covered with concrete, while fallen rain seeps into the ground to become groundwater or flows on the surface of the ground and flows into a river in general. In particular, the method performs calculation using a single stage tank model for an urban area, which mainly deals with surface runoff, and a three-stage series tank model for a non-urban area. Subsequently, in a flow down process, flow of rainwater is calculated, with respect to the rainwater of which the inflow amount into a river is calculated using the runoff process. In the method, in order to calculate the flow of the rainwater in the flow down process, a river channel in a 5-km lattice element is partitioned into six areas along the course of the river, and temporal fluctuation in the amount of flowing-down rainwater is calculated.

A flood disaster (such as swelling and flooding of a river) caused by heavy rain has a higher occurrence probability as the amount of flowing-down rainwater increases, and it is required to consider a time lag before rain having fallen upstream converges downstream. The basin water index is, as an index devised with the above requirements taken into consideration, used for a criterion for issuance of flood warning and advisory which meteorological observatories in various regions issue.

Techniques for estimating moisture content at the ground surface over a wide area include a technique described in NPL 2. In addition, NPL 3 describes a technique for calculating a degree of risk at which a landslide disaster may occur from moisture content in soil.

CITATION LIST

Patent Literature

[PTL 1] JP 5537883 B

Non Patent Literature

[NPL 1] Nobuyuki Tanaka et al., "Flood Warning/Advisory Improvement based on JMA Runoff Index", Weather Service Bulletin, Vol. 75, No. 2, 2008, p. 35-69
[NPL 2] Kentaro Aida et al., "Study on Development of a Frequently Applicable SAR Algorithm for Soil Moisture using ALOS/PALSAR", Proceeding of the Japanese Conference on Hydraulics, Vol. 70, No. 4, 2014, I_589-I_594
[NPL 3] Shinji Kasahara et al., "Study of the Slope Stability Analysis Technique using Real-time Measuring Sensor (1)", Proceedings of the 2015 IEICE General Conference, 2015, A-18-4

SUMMARY OF INVENTION

Technical Problem

There is a problem in that the method of predicting a landslide disaster and a flood disaster using a soil water index or a basin water index each calculated based on the amount of rainfall, as described in PTL 1 and NPL 1, is not sufficient in prediction accuracy, although the method is capable of performing prediction across a wide area. This is because moisture content and a risk of disaster occurrence are calculated based on only the amount of rainfall. On the other hand, when moisture content is to be measured directly using sensors such as a soil moisture meter, there is a problem in that measurement cannot be performed at a location where it is difficult to place a sensor exists. As a result, there is a problem in that it is difficult to achieve prediction accuracy and wide coverage at the same time in predicting a disaster caused by rainfall such as a landslide disaster or a flood disaster.

In addition, although the algorithm of estimating moisture content at the ground surface over a wide area described in NPL 2 is capable of estimating moisture content at the ground surface across a wide area, the algorithm is insufficient in estimation accuracy, and has a problem in that it is difficult to calculate a degree of risk of a disaster with high accuracy based on only estimated moisture content at the ground surface. Note that, in terms of being required to calculate moisture content in soil with high accuracy, a similar problem applies to the method described in NPL 3.

Accordingly, an object of the present invention is to provide a disaster prediction system, a moisture prediction device, a disaster prediction method, and a disaster prediction program recording medium that are capable of achieving prediction across a wide area with high accuracy for a disaster caused by rainfall such as a landslide disaster or a flood disaster.

Solution to Problem

A disaster prediction system according to the present invention includes: soil moisture acquisition means for acquiring amount of moisture in soil at a specified site, ground surface moisture acquisition means for acquiring amount of moisture at a ground surface within a given range including the specified site, and estimation means for estimating amount of moisture in soil at a freely-selected site in the given range or a parameter indicating a property of soil at the freely-selected site in the given range, based on the amount of moisture in the soil at the specified site and the amount of moisture at the ground surface within the given range.

A moisture prediction device according to the present invention includes: soil moisture acquisition means for acquiring amount of moisture in soil at a specified site, ground surface moisture acquisition means for acquiring the amount of moisture at a ground surface within a given range that includes the specified site, and estimation means for estimating amount of moisture in soil at a freely-selected site in the given range or a parameter indicating a property of soil at the freely-selected site in the given range based on the amount of moisture in soil at the specified site and the amount of moisture at the ground surface within the given range.

A disaster prediction method according to the present invention includes: acquiring, by an information processing device, amount of moisture in soil at a specified site, acquiring, by the information processing device, amount of moisture at a ground surface within a given range that includes the specified site, and estimating, by the information processing device, amount of moisture in soil at a freely-selected site in the given range or a parameter that indicates a property of soil at the freely-selected site in the given range based on the amount of moisture in soil at the specified site and the amount of moisture at the ground surface within the given range.

A disaster prediction program recording medium according to the present invention records a program that causes a computer to execute: processing of acquiring amount of moisture in soil at a specified site, processing of acquiring amount of moisture at a ground surface within a given range that includes the specified site, and processing of estimating amount of moisture in soil at a freely-selected site in the given range or a parameter that indicates a property of soil at the freely-selected site in the given range, based on the amount of moisture in soil at the specified site and the amount of moisture at the ground surface within the given range.

Advantageous Effects of Invention

According to the present invention, prediction across a wide area with high accuracy for a disaster caused by rainfall such as a landslide disaster and a flood disaster can be achieved.

DESCRIPTION OF EMBODIMENTS

Figure 2:
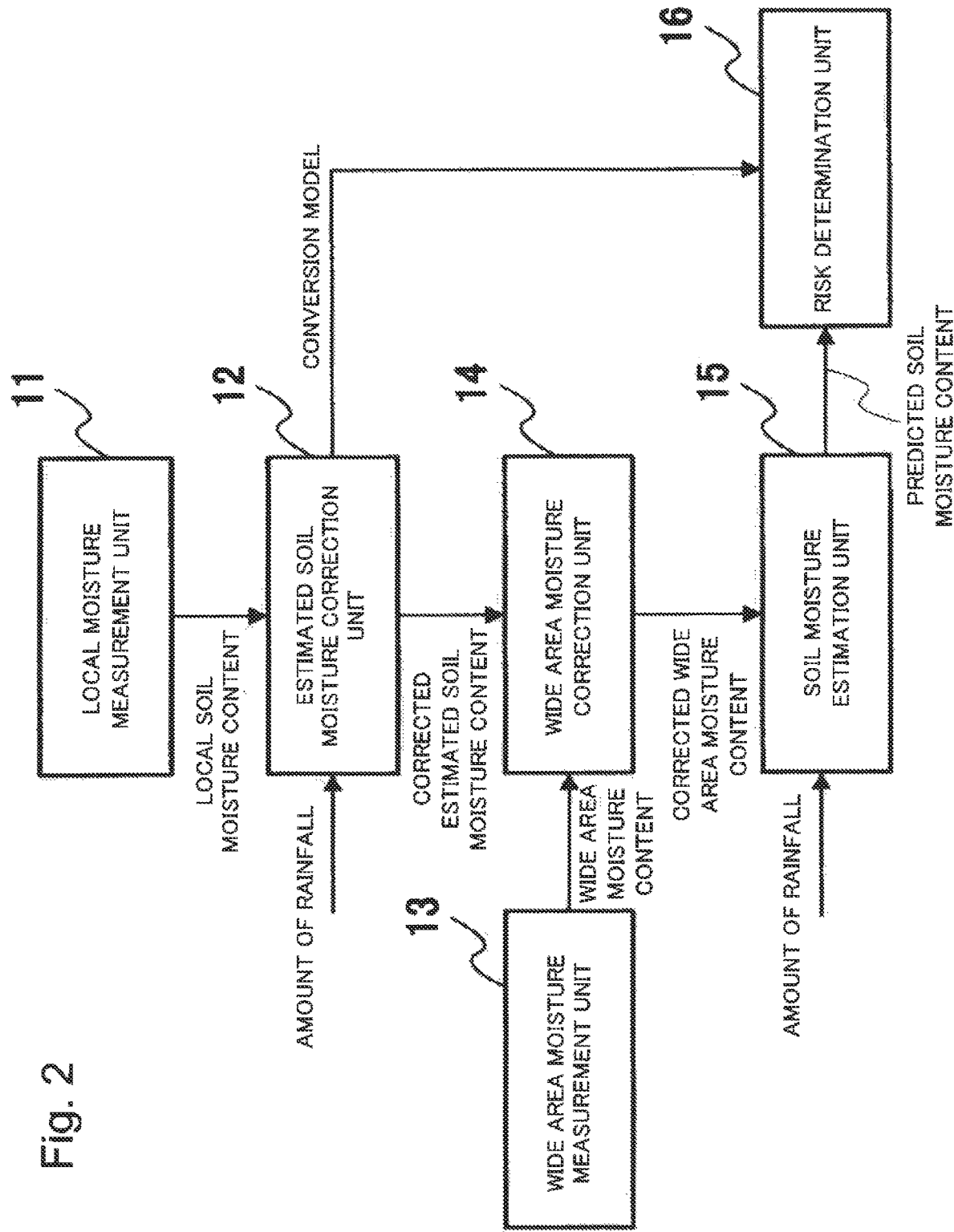
FIG. 2 is a block diagram illustrating a configuration example of a disaster prediction system of a first example embodiment.

Hereinafter, an example embodiment of the present invention will be described with reference to the drawings. FIG. 2 is a block diagram illustrating a configuration example of a disaster prediction system of a first example embodiment. The disaster prediction system illustrated in FIG. 2 includes a local moisture measurement unit 11, an estimated soil moisture correction unit 12, a wide area moisture measurement unit 13, a wide area moisture correction unit 14, a soil moisture estimation unit 15, and a risk determination unit 16.

The disaster prediction system of the present example embodiment may be configured by combining, for example, an information processing device such as a server device and a personal computer, a ground surface observation device that is mountable on a satellite or an aircraft such as a synthetic aperture radar (SAR), and a measurement device such as a soil moisture meter. In addition, the each processing units that the disaster prediction system includes (the estimated soil moisture correction unit 12, the wide area moisture correction unit 14, the soil moisture estimation unit 15, and the risk determination unit 16) may be implemented by, for example, a processor reading a program stored in a storage area and the like and executing it in an information processing device and the like.

The local moisture measurement unit 11 outputs local soil moisture content that is the amount of moisture in soil measured directly in a specific local area. The local moisture measurement unit 11 is implemented by, for example, one or more sensors such as a soil moisture meter that are installed in the specific local area and an information processing device and the like connected thereto. In the above configuration, the sensors are not limited to a soil moisture meter and may be any sensor that is capable of measuring moisture content in soil, such as a vibration sensor. In addition, when moisture content in soil is measured using the sensors, it is preferable that, moisture content at a plurality of depths are measured, such as at 10 cm, 30 cm, and 50 cm from the ground surface, considering that strata vary according to depth from a ground surface. Further, it is preferable that a plurality of sensors described above be installed at intervals in the targeted area. Hereinafter, there is a case such that a specific local area in which the local moisture measurement unit 11 measures is referred to as a first area. Note that a plurality of the first areas may be set. In addition, it is assumed that the first area in the present example embodiment is an area with similar soil property.

Information output by the local moisture measurement unit 11 may include, in addition to the local soil moisture content, information of locations at which the sensors are installed. The information of locations may be latitudes and longitudes of the locations at which the sensors are installed, information of directions and distances of the locations from any object that serves as a mark, or other information. The information output by the local moisture measurement unit 11 may also include, in addition to the local soil moisture content, information of water level and water volume of a river to which water in the ground in the first area runs off, which are measured by one or more sensors such as a water level gauge installed at the river.

The estimated soil moisture correction unit 12 corrects the estimated soil moisture content, based on the local soil moisture content in the first area output by the local moisture measurement unit 11 and estimated soil moisture content that is soil moisture content in each mesh element in an area including the first area, the estimated soil moisture being estimated based on information of the amount of rainfall measured by a rain gauge and the like. The estimated soil moisture correction unit 12 may modify parameters (for example, parameters indicating the property of soil and the like) which are used when calculating the estimated soil moisture content with respect to each mesh element, in such a way that the estimated soil moisture content comes close to the local soil moisture content in the mesh element in which the local soil moisture content was measured, for example. In this case, the estimated soil moisture correction unit 12 may set estimated soil moisture content calculated using parameters after modification as corrected estimated soil moisture content, that is estimated soil moisture content after correction in the mesh element. In addition, the estimated soil moisture correction unit 12 may generate and output a conversion model that converts, with respect to a freely-selected site, the corrected estimated soil moisture content to soil moisture content (local soil moisture content) that would be measured if a sensor were installed at the point.

Hereinafter, description will be made using a specific example. In the following description, an example will be described in which the estimated soil moisture correction unit 12 calculates (estimates) soil moisture content in an area including the first area, using a soil water index, based on the amount of rainfall. For example, the estimated soil moisture correction unit 12 may partition the area including the first area into mesh elements of a predetermined size, and consider the storage amount in tanks in each mesh element as the moisture content in soil in the mesh element. In this case, the storage amount in the tanks in each mesh element is the estimated soil moisture content in the mesh element. In the present example, three types of information, including a runoff coefficient that indicates a rate at which water runs off from a runoff outlet on the side face of a tank to surrounding soil, a seepage coefficient that indicates seepage of water from a seepage runoff outlet on the bottom face into a deeper portion, and height above the bottom face to the runoff outlet of the tank, are equivalent to the parameters indicating the property of soil in the area.

Water in a mesh element runs off mainly in a steepest direction of gradient of inclination of the ground surface in the periphery of the mesh element. Therefore, in mesh elements located in the runoff direction, inflow and runoff are calculated in consideration of water flowed from other mesh elements. In this manner, the estimated soil moisture correction unit 12 calculates water flow in a chain. Moisture content in soil for each mesh element may be estimated using parameters that are considered to be appropriate in a tank model as described in NPL 1, for example. The estimated soil moisture correction unit 12 may update the parameters by matching the estimated soil moisture content estimated in a manner described above with the local soil moisture content measured by the local moisture measurement unit 11, and by using a method such as a data assimilation. Note that the property parameters of soil are not limited to the above-described three types of information. For example, angle of a slope, influence of vegetation, and the like may be used in determining the runoff coefficient, the seepage coefficient, and the height above the bottom face to the runoff outlet of a tank.

In addition, when information of the water level and water volume of a river to which water in the ground in the first area runs off is additionally output from the local moisture measurement unit 11, the estimated soil moisture correction unit 12 may update the parameters used for the estimation of soil moisture content, by further matching the information of water level and water volume with a water level and water volume of the river calculated based on the amount of water that runs off from the first area to the river, using a method such as data assimilation. In this update, the parameters are updated to more optimal parameters by comparing the local soil moisture content measured by the local moisture measurement unit 11 with the estimated soil moisture content in a mesh element including the site at which the local soil moisture content was measured out of the estimated soil moisture content in all mesh elements estimated using the tank model, and, in addition, the soil moisture content (estimated soil moisture content) for each mesh element is also updated. Note that, in this example, estimated soil moisture content after update for each mesh element may be set as the corrected estimated soil moisture content.

Further, in this example, the estimated soil moisture correction unit 12 may generate a conversion model that converts the corrected estimated soil moisture content at a freely-selected site to soil moisture content (local soil moisture content) that would be measured if a sensor were placed at the site, using the local soil moisture content that the local moisture measurement unit 11 measured and soil moisture content (estimated soil moisture content) after correction for the mesh element where the local soil moisture content was measured.

Examples of a generation method of the conversion model include, for example, a method for modeling, with respect to all mesh elements for which the local soil moisture content and the estimated soil moisture content are matched with each other, a relationship between the respective soil moisture content with a linear expression that minimizes the square sum of distances from respective pieces of data when two indices, the local soil moisture content and the corrected estimated soil moisture content, are assigned to the vertical axis and the horizontal axis respectively. Note that the generation method of the conversion model is not limited to the above-described method, and other methods may be employed.

Note that, in the processing of correcting the property parameters of soil for each mesh element, the property parameters with respect to mesh elements, that do not include a point at which the local moisture measurement unit 11 measured local soil moisture content, may be assumed to be the same as those in a most adjacent mesh element under the assumption that the property parameters of soil scarcely varies when the mesh elements are adjacent to one another, may be assumed to be averages of the property parameters of soil in adjacent mesh elements, or may be complemented by other methods. In addition, when calculating a degree of risk of a flood disaster, the estimated soil moisture correction unit 12 may omit the generation and output of a conversion model.

In addition, so as to be able to successively correct the estimated soil moisture content as described above, the disaster prediction system may store information output by the local moisture measurement unit 11 (the local soil moisture content, information relating to the water level and water volume of a river, or the like) in a not-illustrated database and the like.

The wide area moisture measurement unit 13 measures or estimates, from an observation result obtained by observing the ground surface of a wide area including at least the first area, wide area moisture correlation quantity, which is a quantity having a correlation with moisture content at the ground surface or the soil moisture content and having geographical continuity across the wide area, and outputs the wide area moisture correlation quantity as wide area ground surface moisture content. Note that the moisture content at the ground surface can be said to be a type of wide area moisture correlation quantity, because the moisture content at the ground surface also has a correlation with the soil moisture content in the above-described tank model, and because the moisture content at the ground surface has geographical continuity in the sense that the value thereof in an area influences values in proximate areas. In addition, the ground surface in the above description may include a surface layer portion within a range in which data can be acquired by observation, not limited to the surface of the ground.

The wide area moisture measurement unit 13 may estimate, for example, the moisture content at the ground surface using observed images and the like obtained by observing the ground surface by use of a SAR and the like from a satellite or an aircraft, and output the moisture content at the ground as the wide area ground surface moisture content. Examples of a method for estimating the moisture content at the ground surface from an observation result by a SAR include, for example, a method described in NPL 2. In addition, observed images acquired using a SAR and the like enable information of light intensity to be acquired that indirectly includes information of property data of soil, such as the size of grains of soil or ground surface components on the ground surface, or the extent of vegetation, both of which influence reflected waves. Use of such information enables an estimation of the moisture content at the ground surface in consideration of the property of soil. Note that the wide area moisture measurement unit 13 may estimate the moisture content at the ground surface and the wide area moisture correlation quantity using a method other than the method described in NPL 2. In addition, although the following description will be made using a case where the moisture content at the ground surface is output as the wide area ground surface moisture content as an example, the similar operation in the following description basically applies to a case even where another type of wide area moisture correlation quantity different from the wide area ground surface moisture content is output.

The wide area moisture correction unit 14 corrects the moisture content at the ground surface for each mesh element by matching the corrected estimated soil moisture content for each mesh element which is output from the estimated soil moisture correction unit 12, with the moisture content at the ground surface for each mesh element indicated by the wide area ground surface moisture content which is output from the wide area moisture measurement unit 13. The wide area moisture correction unit 14 subsequently outputs moisture content at the ground surface after correction for each mesh element as corrected wide area ground surface moisture content.

Hereinafter, description will be made using a specific example. In the following description, an example of a case such that the corrected estimated soil moisture content, which is output from the estimated soil moisture correction unit 12, includes various types of moisture content in soil calculated using tanks stacked in three stages in each mesh element will be described. In this case, it is considered that the amount of storage in the first stage tank which indicates a state of the ground close to the surface layer portion and the moisture content at the ground surface have substantially equivalent amount or have a strong correlation with each other even when not having the equivalent amount. Thus, it is also considered that the estimated amount of storage in the first stage tank for each mesh element and the moisture content at the ground surface in the mesh element, indicated by the wide area ground surface moisture content estimated from an observation result by the SAR, have substantially equivalent amount or have a strong correlation even when not having the equivalent amount. Therefore, the wide area moisture correction unit 14 may correct the wide area ground surface moisture content (more specifically, the moisture content at the ground surface and the like in the whole area) by matching the amounts of storage in the first stage tanks (moisture content in the surface layer) in mesh elements in the first area among information obtained as the corrected estimated soil moisture content for each mesh element with the moisture content at the ground surface in an area that overlaps the mesh elements most widely among information obtained as the wide area ground surface moisture content, using a method such as data assimilation. In this correction, the wide area moisture correction unit 14 may model a relationship between the moisture content in the surface layer and the ground surface moisture content in the same area. The relationship can be modeled by either a linear expression or a quadratic expression, and a type of the expression does not matter. In addition, in the modeling, when a moisture meter is installed in the surface layer portion, it is possible to use values from the moisture meter as substitute for the moisture content in the surface layer that the corrected estimated soil moisture content indicates.

In this case, it is assumed that two types of data to be matched with each other are data obtained by observing or estimating moisture content at substantially the same time. Note that whether or not the two times at which the observation or estimation was done are substantially the same may be determined, for example, in such a manner that a difference between the two times is considered to be within an allowable range when the difference is less than or equal to a predetermined time difference (for example, less than or equal to a time interval at which data on the amount of rainfall are observed, such as 5 minutes and 10 minutes).

The wide area moisture correction unit 14 may generate in advance, when correcting the wide area ground surface moisture content, a conversion model that converts the amounts of storage in the first stage tanks in mesh elements in the first area to the moisture contents at the ground surface or the wide area moisture correlation quantity (predetermined quantity having a correlation with the soil moisture content) in an area that overlaps the mesh elements most widely.

Further, the disaster prediction system may store, in a database and the like, information output from the wide area moisture measurement unit 13 (information relating to the ground surface moisture content and the wide area moisture correlation quantity for each pixel of an observed image as wide area ground surface moisture content and an observation region and time, and the like) so as to be able to successively correct the wide area ground surface moisture content as described above.

Note that it is preferable that the disaster prediction system set areas having various soil types as the first areas, which are used for measuring the local soil moisture content, correcting of the estimated soil moisture content (including correction of the property parameters of soil), and correcting the wide area ground surface moisture content in advance. It is also preferable to set the first area by varying, in addition to soil types, patterns of another element that influences the property parameters of soil such as terrain (in particular, angle of inclination of the ground surface) in various ways. The setting causes the measurement of the local soil moisture content, the correction of the estimated soil moisture content (including the correction of the property parameters of soil), and the correction of the wide area ground surface moisture content to be performed on the first areas that are set for various soil types and terrains as a target. In consequence, parameters after correction, a conversion model, and the like that are tailored to various patterns of soil types and terrains may be obtained.

The soil moisture estimation unit 15 estimates the soil moisture content at a freely-selected site where prediction is to be performed, based on moisture content in soil in an area including a prediction site that is the freely-selected site for which prediction is to be performed, which is estimated based on information of the amount of rainfall measured by a rain gauge and the like, and the corrected wide area ground surface moisture content in an area including the second area output by the wide area moisture correction unit 14. In the following description, although, there is a case where an area including the prediction site is referred to as a second area, the second area may be set at any place as long as being within a wide area including the first area.

The soil moisture estimation unit 15 may estimate property parameters of soil for each mesh element in the second area, for example, based on the moisture content in soil in each mesh element in the second area estimated based on the amount of rainfall, and the corrected wide area ground surface moisture content output by the wide area moisture correction unit 14. In addition, the moisture content in soil at the freely-selected site in the second area may be calculated, using the estimated property parameters of soil.

Description will be made using a specific example below. In the following description, it is assumed that the property of soil in the second area has not been known. The soil moisture estimation unit 15 may first estimate the moisture content in soil in each mesh element based on the amount of rainfall, using all conceivable property parameters of soil. In this estimation, when first areas are set for various soil types, the above-described all conceivable property parameters includes the property parameters of soil used for correcting the corrected estimated soil moisture contents based on the local soil moisture content with high accuracy, that is, that enable a value closer to a sensor-measured value to be calculated. The soil moisture estimation unit 15 may estimate the moisture content in soil in each mesh element, using such property parameters of soil.

Next, with respect to a mesh element including the prediction site, the soil moisture estimation unit 15 may determine a soil type in which an estimated moisture content at the ground surface (for example, the amount of storage in the first stage tank) indicating a state of the ground close to the surface layer portion, among the estimated moisture content in soil, comes closest to moisture content at the ground surface indicated by the wide area ground surface moisture content after correction in an area including the prediction site, as a soil type at the prediction site. The soil moisture estimation unit 15 may subsequently set a value calculated from property parameters of soil corresponding to the determined soil type and the amount of rainfall as an estimated value of soil moisture content. The soil moisture estimation unit 15 may estimate a total value of the amounts of storage in the first to third stage tanks in the tank model obtained from the property parameters of soil corresponding to the determined soil type and the amount of rainfall as, for example, soil moisture content at the prediction site.

Note that, when the wide area moisture correction unit 14 generates a conversion model that converts the amounts of storage in the first stage tanks in mesh elements to ground surface moisture content in an area that overlaps the mesh elements most widely (for example, a pixel in an observed image by a SAR) for each soil type, the amount of storage in the first stage tank and the ground surface moisture content may be associated with each other using the conversion model.

Note that the soil moisture estimation unit 15 can also estimate the soil moisture content for each mesh element in the second area without determining the property parameters of soil. For example, the soil moisture estimation unit 15 may obtain, as a conversion parameter at a freely-selected site, a difference between the local soil moisture content or the corrected estimated soil moisture content, both of which are considered to be comparable to the local moisture content, and the ground surface moisture content indicated by the wide area ground surface moisture content at which the local soil moisture content was measured or the wide area ground surface moisture content after correction. In such a case, with respect to the freely-selected site, the soil moisture estimation unit 15 may estimate as soil moisture content at the site, a value calculated by adding the calculated difference to the ground surface moisture content indicated by the wide area ground surface moisture content at the site or the wide area ground surface moisture content after correction. In addition, the soil moisture estimation unit 15 may obtain, as a conversion parameter at the freely-selected site, a ratio of the ground surface moisture content at the site to the local soil moisture content or the corrected estimated soil moisture content which is considered to be comparable to the local moisture content, instead of the difference. In such a case, with respect to the freely-selected site, the soil moisture estimation unit 15 may estimate, as soil moisture content at the site, a value calculated by dividing the ground surface moisture content indicated by the wide area ground surface moisture content at the site or the wide area ground surface moisture content after correction by the calculated ratio.

In the latter case, since the soil moisture estimation unit 15 is considered to be estimating moisture content in the first stage tank in the tank model, it is also possible to calculate various types of data, such as water volume running off from the respective tanks and water volume flowing in the respective tanks at a freely-selected site, based on the amount of rainfall and parameters opened to the public by the Meteorological Agency and the like. Note that, when the water volume is estimated using this method, the assumption that the parameters of soil are uniform at all sites is to be made. Examples of the parameters that are opened to the public include height of the first runoff outlet [mm], height of the second runoff outlet [mm], and a runoff coefficient [l/hr] with respect to the first stage tank, height of the runoff outlet [mm] and a runoff coefficient [l/hr] with respect to the second stage tank, height of the runoff outlet [mm] and a runoff coefficient [l/hr] with respect to the third stage tank, and the like.

The risk determination unit 16 calculates a degree of risk of occurrence of landslide or flood disasters at the prediction site, based on a conversion model output from the estimated soil moisture correction unit 12 and the soil moisture content at the prediction site output by the soil moisture estimation unit 15. The prediction site may be a plurality of the sites each of which is corresponding to one of the respective mesh elements included in the second area. In such a case, the risk determination unit 16 may calculate degrees of risk of occurrence of landslide or flood disasters may occur at the prediction sites, based on the conversion model output by the estimated soil moisture correction unit 12 and the soil moisture content for each mesh element output by the soil moisture estimation unit 15 at the sites where no sensor is installed.

Figure 1:
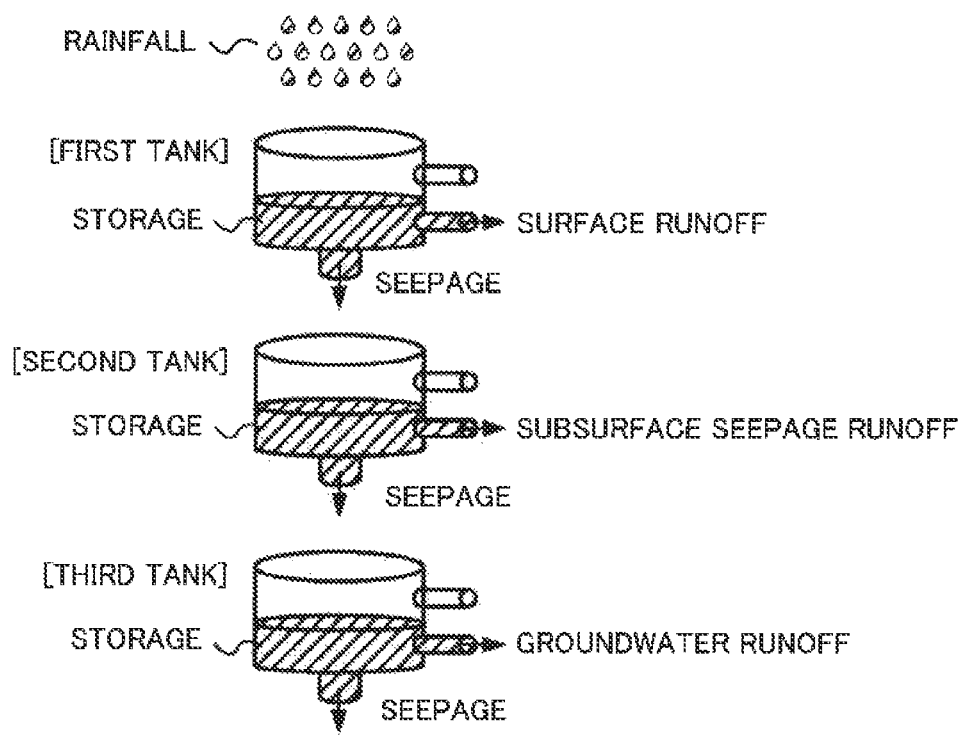
FIG. 1 is a conceptual diagram of a tank model.

When a degree of risk of occurrence of a disaster is calculated, regarding both a landslide disaster and a flood disaster, moisture content in soil running off from the ground surface and the underground at suitable-selected site is often used. For example, with respect to the moisture content running off from the ground surface, information relating to the first stage tank in the tank model (surface runoff in FIG. 1) may be used. In addition, for example, with respect to the moisture content in soil running off from the underground, information relating to the third stage tank in the tank model (groundwater runoff in the drawing) may be used.

The risk determination unit 16 may calculate a measured value that would be measured if a sensor were installed at the prediction site, by converting the soil moisture content at the prediction site output by the soil moisture estimation unit 15 using the conversion model output by the estimated soil moisture correction unit 12. In this case, if the first areas are set for various soil types in the local moisture measurement unit 11 and the estimated soil moisture correction unit 12, it is possible to use a conversion model most suitable for the property of soil at the prediction site.

Note that, when calculating the degree of risk of occurrence of a landslide disaster at a prediction site using the calculated soil moisture content, a slope stability analysis formula and the like described in NPL 3, and the like for example, may be applied. Obviously, the degree of risk of occurrence of a landslide disaster at the prediction site may be calculated by a method other than the above-described method. A specific calculation method of a degree of risk of a landslide disaster and a flood disaster will be described later.

Figure 3:
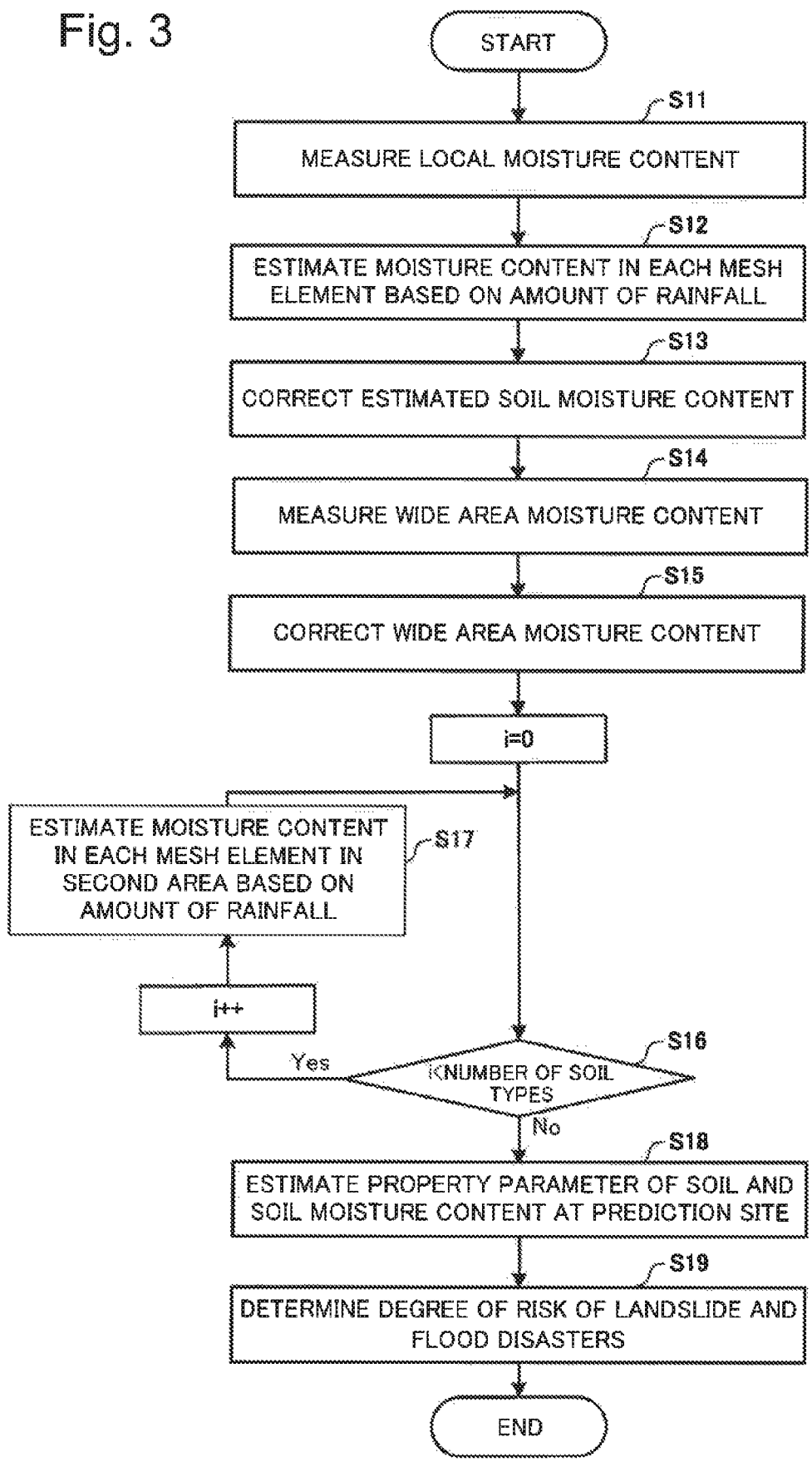
FIG. 3 is a flowchart illustrating an operation example of the disaster prediction system of the first example embodiment.

Next, an operation of the present example embodiment will be described. FIG. 3 is a flowchart illustrating an example of an operation of the disaster prediction system of the present example embodiment.

First, an operation with regard to the first area will be described. In the example illustrated in FIG. 3, first, the local moisture measurement unit 11 measures, via a sensor such as a soil moisture meter installed in a first area, local moisture content, which is the amount of moisture in soil at a site at which the sensor is placed (step S11). The sensor may be installed, for example, in the first area manually.

Next, the estimated soil moisture correction unit 12 estimates soil moisture content in each mesh element in an area including the first area based on the amount of rainfall (step S12). Note that a not-illustrated second soil moisture estimation unit may estimate the estimation of the soil moisture content in each mesh element based on the amount of rainfall. Next, based on the soil moisture content in each mesh element estimated in step S12 and the local moisture content measured in step S11, the estimated soil moisture correction unit 12 corrects property parameters of soil used in estimating soil moisture content (including soil moisture content and moisture content at the ground surface) with respect to each mesh element, and obtains corrected estimated soil moisture content for each mesh element (step S13). In step S13, the estimated soil moisture correction unit 12 generates a conversion model, in conjunction with the corrected estimated soil moisture content, that converts the corrected estimated soil moisture content, obtained by use of parameters after correction based on the amount of rainfall, to soil moisture content that would be measured if a sensor were installed in each mesh element. The above description is a direct operation with respect to at least a site where a sensor is installed.

Next, the wide area moisture measurement unit 13 observes a ground surface for a wide area at least including a prediction site and the first area by means of a SAR and the like, and estimates wide area ground surface moisture content (moisture content at the ground surface or wide area moisture correlation quantity in the wide area) from a result of the observation (step S14).

Next, the wide area moisture correction unit 14 corrects the wide area ground surface moisture content, by matching the corrected estimated soil moisture content (a corrected value of the corrected soil moisture content for each mesh element) obtained in step S13 with the wide area ground surface moisture content (quantity having a correlation with the soil moisture content, such as the moisture content at the ground surface for each mesh element) estimated in step S14 (step S15).

Next, an operation performed with respect to a second area, which is a place where no sensor is installed and includes a freely-selected prediction site, will be described. First, the soil moisture estimation unit 15 estimates moisture content in soil in each mesh element in the second area based on the amount of rainfall using property parameters of all conceivable soil types (steps S16 and S17). In these steps, although it is preferable that a value corresponding to the corrected estimated soil moisture content at the prediction site is estimated moisture content in each mesh element is estimated based on the amount of rainfall with respect to all conceivable property parameters of soil, since the property of soil at the prediction site has not been known.

Next, the soil moisture estimation unit 15 estimates property parameters of soil in the mesh area including the prediction site based on the moisture content in soil in each mesh element for each soil type estimated in step S17, and the wide area ground surface moisture content after correction obtained in step S15. The soil moisture estimation unit 15 subsequently estimates soil moisture content in the area based on the estimated property parameters of soil (step S18).

Finally, the risk determination unit 16 calculates a degree of risk of occurrence of landslide and flood disasters, using the moisture content in soil at the prediction site estimated in step S18 (step S19). In step S19, the risk determination unit 16 may calculate a degree of risk of occurrence of landslide and flood disasters, after converting the moisture content in soil at the prediction site estimated in step S18 to a value to be measured when a sensor is installed at the prediction site, by using the conversion model generated in step S13.

As described above, in the present example embodiment, first, the estimated soil moisture correction unit performs correction so as to bring moisture content estimated based on the amount of rainfall close to a measurement result by the local moisture measurement unit to improve the estimation accuracy of the moisture content. Further, after the wide area ground surface moisture estimation unit corrects moisture content at the ground surface and the like, measured by the wide area ground surface moisture measurement unit across a wide area, so as to bring the moisture content at the ground surface and the like close to the moisture content corrected by the estimated soil moisture correction unit, the soil moisture estimation unit estimates moisture content in soil at a freely-selected site where no sensor is installed with high accuracy, using the moisture content at the ground surface and the like across the wide area corrected by the wide area ground surface moisture correction unit. Employing the configuration as described above enables both prediction accuracy and wide coverage in prediction of a landslide disaster and a flood disaster to be achieved.

More specifically, according to the present example embodiment, moisture content in soil in each mesh element estimated based on the amount of rainfall (estimated soil moisture content) is corrected first, using moisture content in a specified local area directly measured using a sensor such as a soil moisture meter. In the correction, the estimated soil moisture content is corrected in such a way that the estimated soil moisture content comes close to the sensor-measured value. By performing the correction processing on a plurality of soil types, estimation parameters (the above-described property parameters of soil and the like) for estimating the estimated soil moisture content for each mesh element, which are related to the plurality of soil type and based on the amount of rainfall, is corrected so that a value closer to an actually measured value is estimated. Further, according to the present example embodiment, wide area ground surface moisture content such as moisture content at the ground surface, which is acquired by observing a ground surface from a satellite or an aircraft and is estimated across a wide area, is corrected based on the above-described estimated soil moisture content after correction. As a result, it is possible to obtain the wide area ground surface moisture content after correction, which is close to the corrected estimated soil moisture content for each mesh element estimated based on the amount of rainfall, in consideration of a plurality of soil types. In addition, soil moisture content at the prediction site can be obtained with high accuracy using the wide area ground surface moisture content after correction. According to the present example embodiment, since a degree of risk is calculated based on the soil moisture content at the prediction site obtained in a manner as described above, it is possible to achieve both prediction accuracy and wide coverage in prediction of a landslide disaster or a flood disaster.

Further, since a series of steps, including the measurement of soil moisture content by a sensor in the local moisture measurement unit 11, the correction of the property parameters of soil (estimation parameters) in the estimated soil moisture correction unit 12, the measurement of wide area ground surface moisture content in the wide area moisture measurement unit 13, the correction of the wide area ground surface moisture content in the wide area moisture correction unit 14, and the determination of the property parameters of soil in the soil moisture estimation unit 15, is repeated, various parameters are successively corrected in such a way that a value of estimated moisture content comes close to a value of moisture content measured directly by a sensor such as a soil moisture meter, thereby the estimation accuracy of moisture content at a freely-selected site can be improved.

In addition, the soil moisture estimation unit 15 may accept data on a predicted amount of rainfall, in addition to information related to the amount of rainfall measured by a rain gauge. For example, inputting the predicted amount of rainfall at several minutes or several hours later enables the soil moisture estimation unit 15 to calculate a degree of risk of landslide and flood disasters at the future time.

Figure 4:
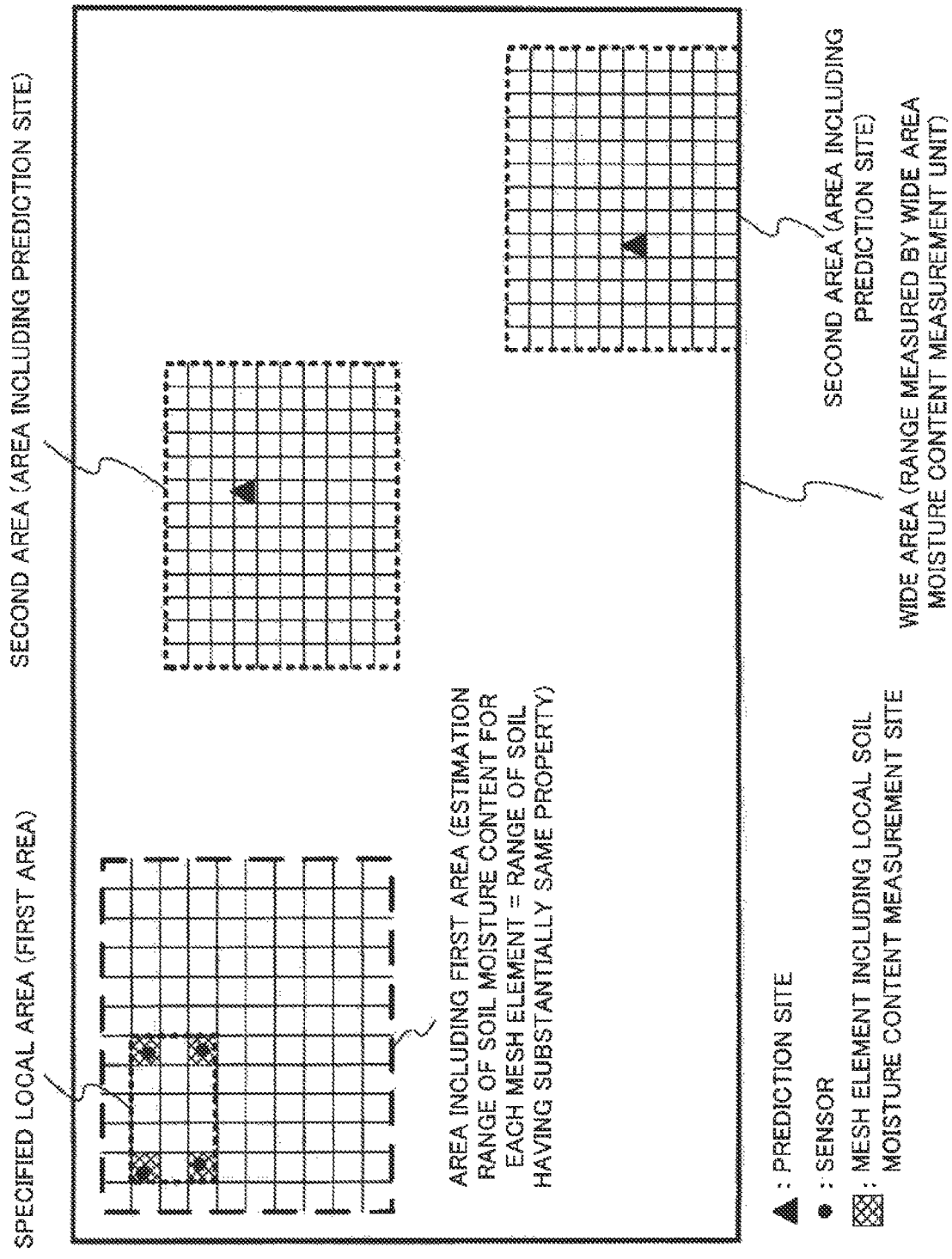
FIG. 4 is an explanatory diagram illustrating an example of area setting.

FIG. 4 is an explanatory diagram illustrating an example of the first area, the meshes, the prediction sites, and the second areas in the present example embodiment. As illustrated in FIG. 4, the first area, which is a specified local area, may be an area in which the property of soil is substantially uniform and including a site where at least one sensor is installed, for example. In this case, when the number of sensors to be installed is one, the first area may be a concept of "site" or may be an area of a single mesh element. In addition, when a plurality of sensors is installed, adjacent placement sites may be grouped into a "first area". In the present example embodiment, with respect to such the first area, by comparing local soil moisture content directly measured with soil moisture content for each mesh element estimated using the amount of precipitation, parameters for each mesh element is corrected so that the estimated soil moisture content in an area including the first area comes close to the measured value, and thus the estimation accuracy of soil moisture content is improved.

In the above, the area including the first area is a range in which the soil moisture content in each mesh element is estimated based on the amount of precipitation. The area including the first area may be a range and the like in which the property of soil and terrain are close or values of the moisture content have continuity, or the area including the first area may have a predetermined fixed size, for example.

In addition, an interval at which sensors are installed (for example, an interval of 50 m) is generally set to be smaller than the size of a mesh used for estimation of soil moisture content (several hundreds of meters to several kilometers). Therefore, when a plurality of sensors is installed in an identical mesh, an average of measured values by the sensors installed in the identical mesh is calculated, or a measured value by a sensor close to the center of the mesh is set as a representative value, and then a value obtained in such a manner may be set as the local soil moisture content.

In addition, the second area including a freely-selected prediction site may be an area included in a range (wide area) which is measured by the wide area moisture measurement unit. In addition, a mesh that is set for the second area may be the same as or different from the mesh set for the first area. Note that the mesh set for the second area may be an areal unit for measuring the ground surface moisture content (an areal extent corresponding to each pixel of a SAR image and the like).

Note that, mesh width is not limited in both the first area and the second area. For example, mesh width in the first area may be set in a range of dozens of meters to several kilometers. As an example, the mesh width may be 50 m, 250 m, 1 km, or the like. Note that, the smaller the mesh width is, the higher the estimation accuracy of moisture content becomes, while the longer the time becomes. Conversely, the larger the mesh width is, the lower the estimation accuracy of moisture content becomes, while the shorter calculation time becomes.

Figure 5:
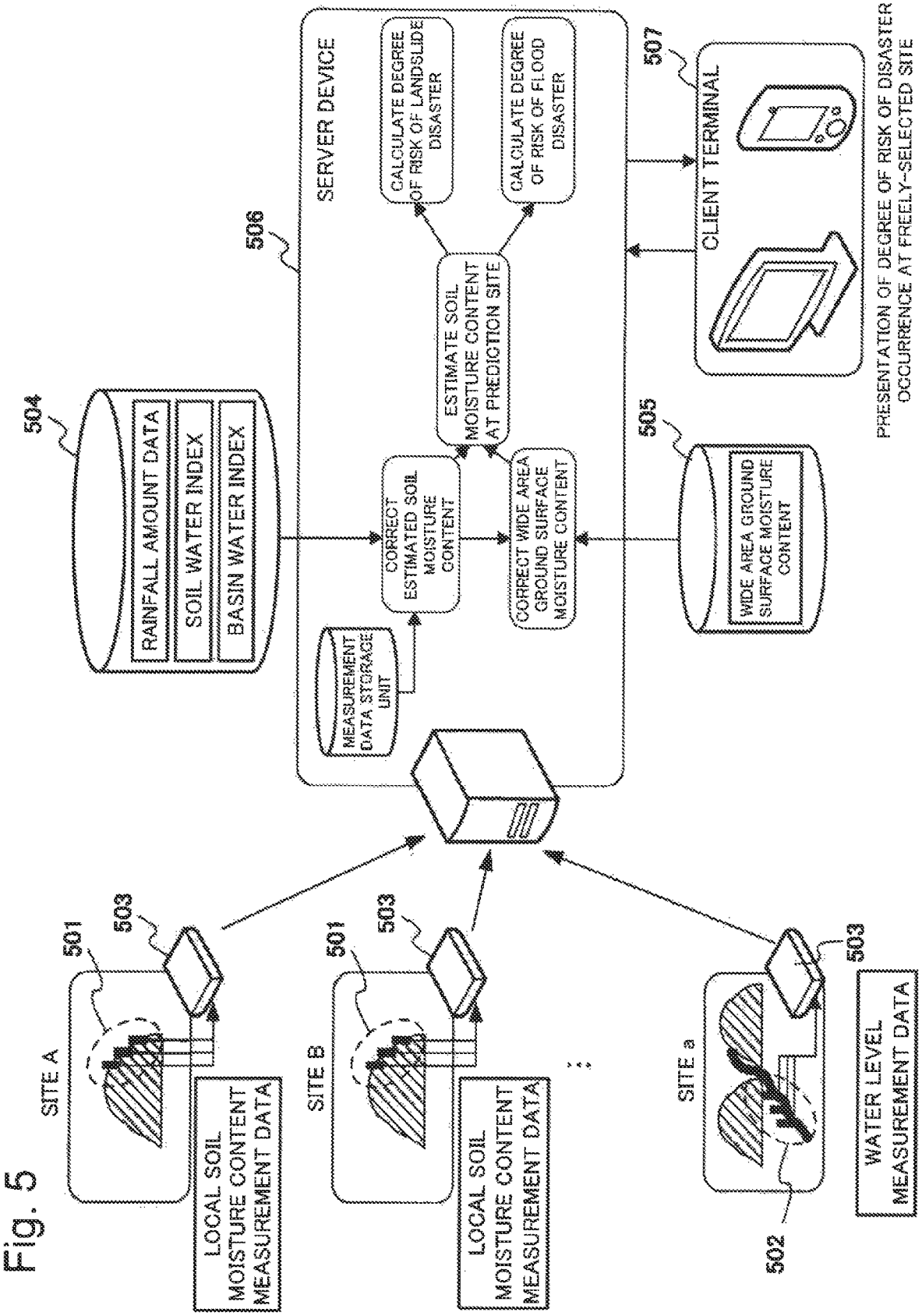
FIG. 5 is a block diagram illustrating a system configuration example of the disaster prediction system.

FIG. 5 is a conceptual diagram illustrating a system configuration example and a data flow of the disaster prediction system. In the example illustrated in FIG. 5, local soil moisture content, water level of a river, and the like are measured by sensors such as a soil moisture meter 501 or a water level gauge 502. In the example, data measured by the each sensors in each first area are transmitted to a relay device 503, which is set in the first area. In the data transmission, each sensor may transmit the measured data to the relay device 503 wirelessly when the sensor is equipped with a wireless communication function, or by means of wired communication. Measurement as described above are performed in a plurality of the first areas (site A, site B, site a, and the like in the drawing) related to a plurality of soil types, and information relating to the soil moisture content or the water level and water volume of a river measured in each area is transmitted from the relay device 503 in each of the area to a server device 506.

In addition, information relating to the position of a location where a degree of risk of a disaster is expected to be obtained is transmitted from a client terminal 507, such as a personal computer and a mobile phone, to the server device 506. In the above, the information relating to a position may be information of the position represented in latitude and longitude, or information of a location that has a certain area such as a town name and a city name.

The server device 506, while storing the measured data individually transmitted from the relay devices 503 and the like, performs respective processing including the correction of local soil moisture content, the correction of the wide area ground surface moisture content, the estimation of the soil moisture content in the second area including the prediction site where no sensor is installed, the calculation of a degree of risk of a landslide disaster, and the calculation of a degree of risk of a flood disaster, by using the measured data, rainfall amount data indicating information of the amount of rainfall measured by a rain gauge and the like, and the measured data on the wide area ground surface moisture content measured by a SAR and the like. In the above processing, when the measured data transmitted from the relay devices 503 and the like are stored, the measured data may be stored inside the server device 506 or in an external storage medium accessible from the server device 506.

The rainfall amount data and the measured data on the wide area ground surface moisture content may be stored in a database and the like. The database and the like may be set up inside the server device 506 or outside the server device 506.

The server device 506 may calculate a degree of risk of landslide and flood disasters with respect to a position specified by the client terminal 507, and transmit information relating to the degree of risk to the client terminal 507. In the above description, although a position where a degree of risk is expected to be calculated is specified by the client side, it is also possible to calculate the degrees of risk with respect to all areas or specified areas included in the wide area, and to inform people present around a base station of the degree of disaster risk concerning each area, by associating the calculated degrees of risk with information of the base stations of the mobile phone network. Note that the configuration illustrated in FIG. 5 is an example of the configuration of the disaster prediction system, and is not limited thereto. In other words, the disaster prediction system may be configured using other methods and other components.

As already described, in the present example embodiment, the estimated soil moisture correction unit 12 improves the estimation accuracy of the moisture content calculated based on the amount of rainfall, and the wide area moisture correction unit 14 improves the estimation accuracy of the moisture content at the ground surface across a wide area. Then, the soil moisture estimation unit 15 estimates the moisture content in soil at freely-selected site. Employing the method described above achieves estimation of the soil moisture content with higher accuracy than a method of estimating the soil moisture content only from the amount of rainfall.

In addition, according to the present example embodiment, the amounts of storage in the first to third tanks can accurately monitored in prediction using a soil water index such as the prediction of a landslide disaster.

However, even when the soil water index itself does not differ, since increase in a degree of risk of occurrence of a landslide disaster differs area by area depending on influence of terrain, geographical features, and the like, it is effective to use a slope stability analysis formula that is represented by the following formula (1), also described in NPL 3, in calculating the degree of risk.

[Math. 1]

$$Fs = \frac{\sum \{cl + (W - ub)\cos\alpha \cdot \tan\varphi\}}{\sum W \sin\alpha} \quad (1)$$

In the formula (1), W denotes clod weight, c denotes cohesion, u denotes pore water pressure, and φ denotes an internal friction angle, respectively. Note also that α denotes an inclination angle of a slope, l denotes sliding surface length, and b denotes width of a slice. The formula (1) can be considered to be a formula for obtaining a safety factor Fs of a slope based on the four variables (W, c, u, and φ), which are influenced by soil texture itself, and other constants. It is known that the variables W and u vary depending on a moisture ratio of soil, and the variables c and φ decrease as the moisture ratio increases when the moisture ratio is greater than an optimum moisture ratio at which strength of soil takes a maximum. Based on these relations, relations between the above-described four parameters and the moisture content can be modeled in advance. Use of such a model prescribing relation between the respective parameters and moisture content enables a safety factor Fs of every hour at a freely-selected site to be calculated. Note that, although the above-described formula (1) is an example of a slope stability analysis formula referred to as Fellenius method (modified Fellenius method), the slope stability analysis formula is not limited to the Fellenius method. For example, in addition to the Fellenius method, a Bishop method, a Janbu method, a slope stability analysis formula proposed by Okimura et al. (1985), a slope stability analysis formula by Nash (1987), a slope stability analysis formula proposed by Taylor et al. (2007), a slope stability analysis formula proposed by Rossi et al. (2012), and the like may be used. Parameters influenced by soil texture itself in all the above methods can be considered to be similar as those in the Fellenius method. In addition, Σ represents taking the sum with respect to slices composing a slope. In the present example embodiment, the number of slices may be one or plural. For example, when a degree of risk is calculated with respect to a specified site or a specified mesh element, the degree of risk (safety factor Fs) may be calculated using the above-described formula (1) and the like, assuming that a mesh element including the site or the specified mesh element is only the slice composing a slope. In addition, when a degree of risk is calculated with respect to an area or a region having a certain width, the degree of risk (safety factor Fs) may be calculated using the above-described formula (1) and the like, assuming that respective mesh elements included in the region are slices composing a slope.

In addition, according to the present example embodiment, the amounts of storage in the tanks in the tank model, that is, moisture content in soil, can be estimated more accurately, a safety factor using a slope stability analysis formula may also be calculated with high accuracy. In the slope stability analysis formula, a slope is defined as safe if Fs>1 holds, and is defined as having a risk if Fs≤1 holds. It may be determined that there is a risk of a landslide disaster in an area concerned, at a point where Fs decreases gradually and comes close to 1. Issuing an evacuation recommendation or an evacuation instruction to residents living in the surrounding area of the site in such a case enables a timely warning without missing an opportunity.

Further, according to the present example embodiment, runoff calculation using a distributed runoff model that performs runoff analysis of water running off from a basin partitioned into mesh elements, which is frequently used for prediction of a flood disaster, is performed finely. Specifically, runoff volume of water from the rainfall for any point can be calculated more accurately in a runoff process in prediction using a basin water index, in other words, a process in which rain having fallen on a surface of the ground seeps into the ground to become groundwater or flows on a surface of the ground and finally flows into a river. This is because both the runoff volume of groundwater, which is represented as runoff volume from the third tank in the tank model, and the runoff volume on the surface of the ground, which is represented as runoff volume from the first tank, can be calculated more accurately.

Therefore, temporal variation in the amount of rainwater can be assessed more accurately by use of a kinematic wave method and the like in a flow down process, that is, a process in which rainwater flowed into a river through a runoff process flows down along the river. Then, in addition to water volume running off directly to a river as water flowing on the surface of the ground or as groundwater, it is possible to calculate runoff volume to the river from tributaries that flow into the river, with respect to the river for which water level and water volume thereof are expected to be obtained. According to this capability, a flow rate of water of every hour flowing into any river can be obtained, including small-and-medium-sized rivers with no water level gauge installed.

For example, the system may set a threshold to determine water level or water volume deemed at risk for a freely-selected site in each river in advance, define a value obtained by subtracting the threshold from a present water level or water volume as a degree of risk, and when the degree of risk reaches a value greater than or equal to a certain value, determine that there is a risk of a flood at the site. Issuing an evacuation recommendation or an evacuation instruction to local residents in such a case enables timely warning without missing an opportunity. Note that other methods may be used for calculating the degree of risk of a landslide disaster or a flood disaster.

Figure 6:
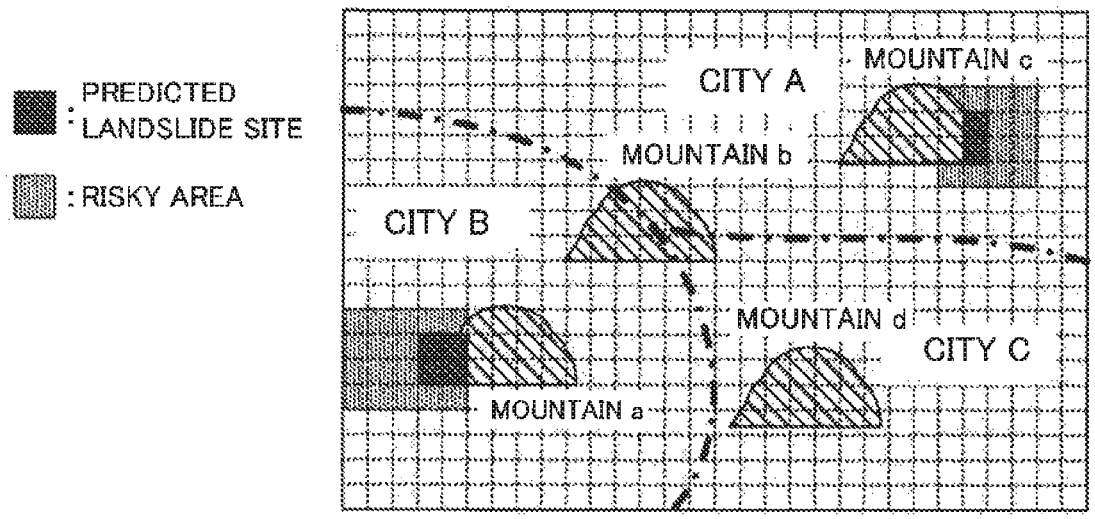
FIG. 6 is an explanatory diagram illustrating a presentation example of degrees of risk of landslide disasters.
Figure 7:
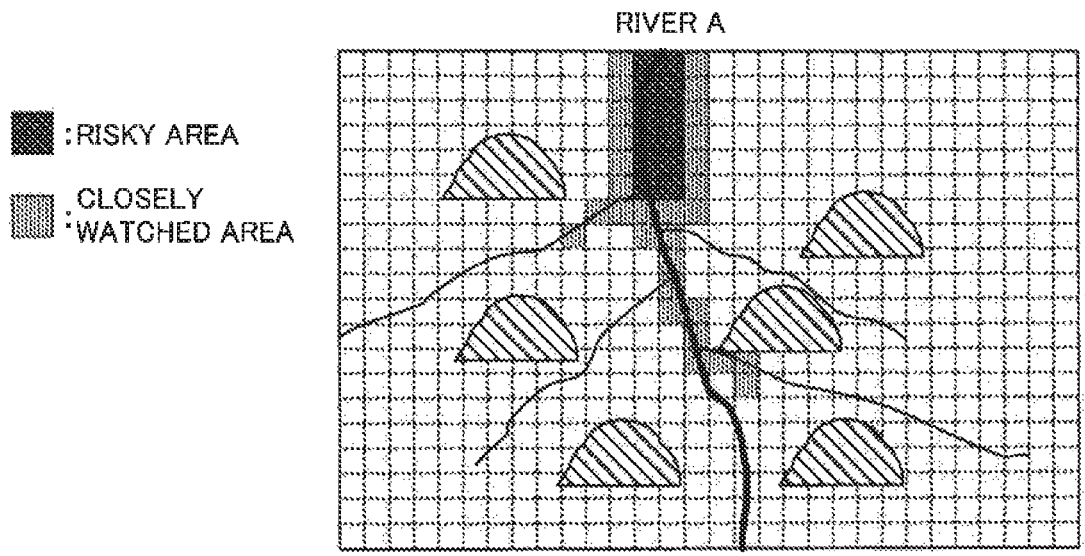
FIG. 7 is an explanatory diagram illustrating a presentation example of a degree of risk of a flood disaster.

FIGS. 6 and 7 are explanatory diagrams illustrating examples of information communication such as warning based on the calculated degree of risk of a landslide disaster and degree of risk of a flood disaster.

For example, when presenting a degree of risk of a landslide disaster, the system may calculate a safety factor for each mesh element by means of a slope stability analysis formula, and as illustrated in FIG. 6, generate a map that displays a predicted landslide site and a risky area in a display mode different from that of other areas such as highlighting the predicted landslide site and the risky area, where a site at which the factor of safety is less than or equal to 1 and there is a risk of occurrence of a landslide at a certain time later is specified as the predicted landslide site and a peripheral region of the predicted landslide site is specified as the risky area. In this case, the system may set an extent of the risky area widely in an inclination direction of a slope which is predicted to slide. In addition, the system may classify the degree of risk of a slope into a plurality of risk levels, such as being safe if Fs>1.1 holds, being slightly risky if 0.9<Fs≤1.1 holds, and being substantially risky if Fs≤0.9 holds, and use different display modes corresponding to the levels.

As another example of presentation of the degree of risk of a landslide disaster, the system may generate a map in which the display mode of the risky area is differentiated from other areas, such as colors being differentiated according to a probability of the calculated degree of risk of a disaster. As described above, considering that a certain amount of difference occurs in the calculation accuracy of a degree of risk of a disaster based on moisture content between a mesh element in which moisture content in soil is directly measured using a sensor such as a soil moisture meter and a mesh element in which moisture content in soil is estimated across a wide area using a SAR and the like, such mesh elements may be displayed by distinguishing them. For example, even among the mesh elements determined to be at the same risk level, the system may display a mesh element in which moisture content in soil was directly measured in a heavily shaded manner, whereas display a mesh element in which moisture content in soil was estimated over a wide area in a slightly lighter manner. In addition, the system may distinguish display modes based on colors, instead of light and shade. Further, the system may combine the above-described display methods, for example, weight Fs for mesh elements in which moisture content was estimated across a wide area in such a way that Fs is more heavily weighted as the value of Fs is distanced from 1, and employ display modes according to levels of the values of Fs.

When the system calculated a degree of risk of a disaster based on the predicted amount of rainfall, the system may also present a state at a certain time later. For example, the system may calculate degrees of risk based on the predicted amount of rainfall at different times such as at several minutes later, several tens of minutes later, and several hours later, and employ a display mode that allows the degrees of risk to be switched by a pull-down button and the like.

FIG. 7 illustrates an example of a map for presenting degrees of risk of a flood disaster. For example, the system may calculate water volume when rain having fallen on a slope runs off to a river and flows down along the river, and when the water volume and water level exceed a predetermined level, the system may determine that there exists a risk of a flood in peripheral areas along the river, and display risky areas. As illustrated in FIG. 7, for example, the system may also generate a map in which the display mode of the risky area is differentiated from those of other areas, such as highlighting such a risky area.

In this case, as illustrated in FIG. 7, the areas may be classified by estimated magnitude of damage according to distances from the river. In addition, when presenting the degree of risk of a flood disaster, the system may also generate a map, as with the case of the landslide disaster, which are color-coded according to the probability of a calculated degree of risk of a disaster, and the like. As an example, in the case where it is determined that there exists a risk of a flood disaster, display modes may be differentiated in the light and shade of display between a mesh element in which water level and water volume of a river were measured directly using sensors such as a water level gauge, and a mesh element in which the water level and water volume of the river were estimated across a wide area using such as SAR. Note that the display modes may be differentiated based on colors, instead of light and shade.

When the system calculated a degree of risk of a disaster based on the predicted amount of rainfall, the system may also present a state at a certain time later. For example, the system may calculate degrees of risk based on the predicted amount of rainfall at different times such as at several minutes later, several tens of minutes later, and several hours later, and employ a display mode that allows the degrees of risk to be switched by a pull-down button and the like.

Although omitted in FIGS. 6 and 7, when the system is able to acquire information relating to the latitudes and longitudes of the four vertexes or the center point of a highlighted mesh element, the address of an area corresponding to the mesh element, residents living in the area, and the like, the system may display the information together.

The system may also issue, based on an obtained disaster prediction result (degree of risk), an evacuation recommendation and an evacuation instruction to "Public Information Commons", which is a common base for collecting and sharing information relating to safety and security such as information of a disaster issued by local public entities and the like, and for collectively delivering the information to local residents rapidly and efficiently by way of various media such as television, radio, mobile phone, the Internet, signage, and the like. In addition, the system may send e-mails to target persons, based on the obtained disaster prediction result.

In the present example embodiment, although an example of a system that calculates, by estimating moisture content in soil at the freely-selected site, a degree of risk of a disaster caused by rainfall was described, the system may be achieved as, for example, a moisture prediction device that predicts moisture content at a freely-selected site, by omitting the risk determination unit 16.

Further, the system may be configured in such a way that a processing unit for executing processing of calculating and determining a degree of risk of occurrence of a disaster (for example, the risk determination unit 16), and a processing unit for executing processing of presenting the calculated degree of risk (not illustrated), are configured as separate devices. In such a case, a device implementing the processing unit for executing processing of calculating and determining a degree of risk of occurrence of a disaster (for example, disaster prediction device) may output the calculated degree of risk and a determination result to a device implementing the processing unit for executing processing of presenting the degree of risk (for example, disaster risk degree presentation device). In this case, the disaster risk degree presentation device may output a map and the like for presenting a degree of risk of occurrence of a disaster at each site in a specified area to users.

Figure 8:
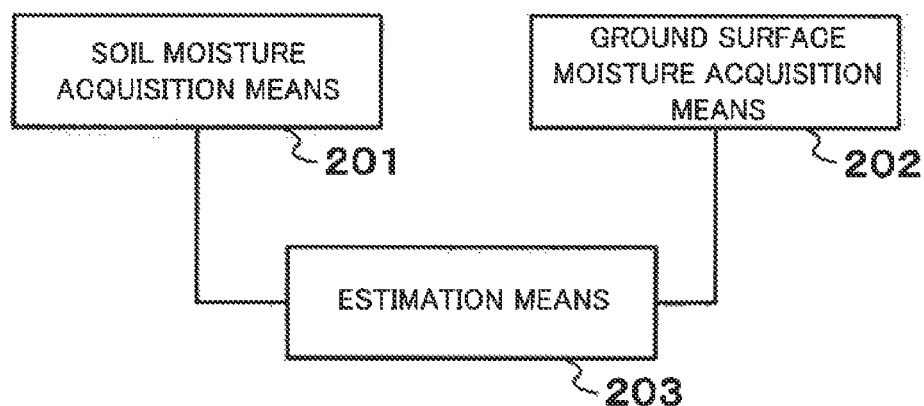
FIG. 8 is a block diagram illustrating an outline of the present invention.

FIG. 8 is a block diagram illustrating an outline of the disaster prediction system in the present invention. As illustrated in FIG. 8, the disaster prediction system in the present invention may include a soil moisture acquisition means 201, a ground surface moisture acquisition means 202, and an estimation means 203.

The soil moisture acquisition means 201 (for example, the local moisture measurement unit 11 or an interface for connection therewith) acquires moisture content in soil at a specified site.

The ground surface moisture acquisition means 202 (for example, the wide area moisture measurement unit 13 or an interface for connection therewith) acquires moisture content at the ground surface within a given range including the specified site.

The estimation means 203 (for example, the soil moisture estimation unit 15) estimates moisture content in soil at a freely-selected site in the given range or a parameter that indicates a property of soil at the freely-selected site in the given range, based on the moisture content in soil at the specified site and the moisture content at the ground surface within the given range.

With a configuration as described above, the moisture content in soil at a freely-selected site can be estimated over a wide range with high accuracy, by thus a disaster caused by the amount of rainfall may be predicted over a wide range with high accuracy.

Note that the estimation means may estimate a parameter that indicates a property of soil at a freely-selected site in the given range based on the moisture content in soil at the specified site and the moisture content at the ground surface within the given range, and estimate moisture content in soil at the freely-selected site in the given range, based on the estimated parameter and the amount of rainfall at the site.

Figure 9:
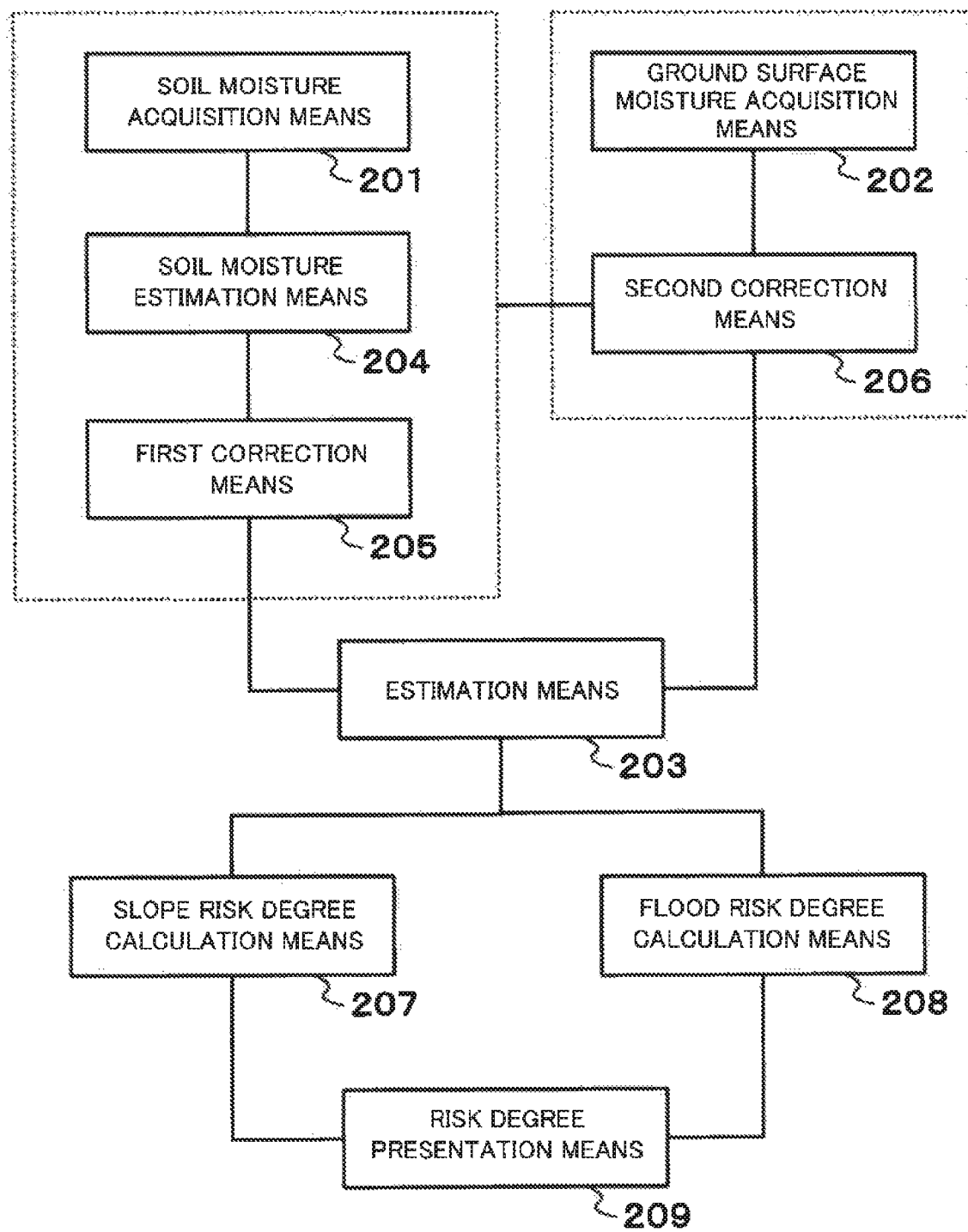
FIG. 9 is a block diagram illustrating another configuration example of the disaster prediction system of the present invention.

FIG. 9 is a block diagram illustrating another configuration example of the disaster prediction system in the present invention. As illustrated in FIG. 9, the disaster prediction system in the present invention may further include a soil moisture estimation means 204 and a first correction means 205. The disaster prediction system may further include a second correction means 206. In addition, the disaster prediction system may further include a slope risk degree calculation means 207, a flood risk degree calculation means 208, and a risk degree presentation means 209.

The soil moisture estimation means 204 (for example, the estimated soil moisture correction unit 12) estimates moisture content in soil in a first area including the specified site, based on the amount of rainfall with respect to each mesh element. In addition, the first correction means 205 (for example, the estimated soil moisture correction unit 12) may correct a parameter used for estimating the moisture content in soil in each mesh element, in such a way as that an estimation result of the moisture content in soil in each mesh element in the first area comes close to the moisture content in soil at the specified site acquired by the soil moisture acquisition means.

Note that, in the above estimation and correction, it is assumed that the first area is set corresponding to at least a plurality of soil types. In addition, the estimation means may estimate moisture content in soil at a freely-selected site in the given range or a parameter indicating a property of soil at the freely-selected site included in a given range, by selecting a parameter after correction corresponding to one soil type, based on moisture content in soil in each mesh element and moisture content at the ground surface in the given range, where moisture content in soil in each mesh element is calculated using parameters after correction corresponding to the plurality of soil types and is based on the amount of rainfall.

In addition, the second correction means 206 (for example, the wide area moisture correction unit 14) may correct a parameter used when measuring the moisture content at the ground surface, in such a way that moisture contents at the ground surface in a given range including the specified site acquired by the ground surface moisture acquisition means comes close to moisture content in soil at the specified site acquired by the soil moisture acquisition means.

In such a case, the estimation means may estimate moisture content in soil at a freely-selected site in the given range, based on moisture content at the ground surface in the given range measured using the parameter after correction.

The above-described parameter may be a parameter indicating a property of soil. In such a case, the estimation means may calculate, using a corrected or estimated parameter that indicates a property of soil, the amount storage and runoff volume of water on the ground surface or in the ground at a freely-selected site in the given range as an estimation result of moisture content in soil.

A relation between the amount of storage of water on the ground surface or in the ground and another variable required for a predetermined slope stability analysis formula may be modeled in advance. In such a case, the slope risk degree calculation means 207 (for example, the risk determination unit 16) may, calculate a degree of risk of a slope by use of the slope stability analysis formula, upon estimating the another variable using the amount of storage of water on the ground surface or in the ground estimated by the estimation means based on the modeled relation. In the above, the degree of risk of a slope may be calculated with respect to each mesh element or an area including a plurality of mesh elements as a target.

The flood risk degree calculation means 208 (for example, the risk determination unit 16) may calculate water volume or water level of every hour of any river to calculate a degree of risk of a flood, based on runoff volume of water on the ground surface or in the ground at a freely-selected site.

The risk degree presentation means 209 may perform processing of displaying, on a user terminal, a degree of risk of a disaster caused by the amount of rainfall including a degree of risk of a slope or a degree of risk of a flood.

The present invention has been described with referring to an example embodiment and example thereof. However, the present invention is not limited to the example embodiment and example described above. Various modifications in the configurations or details in the present invention that could be understood by a person skilled in the art may be applied within the scope of the present invention.

This application claims priority based on Japanese Patent Application No. 2015-180291, filed on Sep. 14, 2015, the entire disclosure of which is incorporated herein by reference.

INDUSTRIAL APPLICABILITY

The present invention is suitably applicable to disaster prediction based on soil moisture content, in particular, soil moisture content across a wide area.

REFERENCE SIGNS LIST

11 Local moisture measurement unit
12. Estimated soil moisture correction unit
13 Wide area moisture measurement unit
14 Wide area moisture correction unit
15 Soil moisture estimation unit
16 Risk determination unit
501 Soil moisture meter
502 Water level gauge
503 Relay device
504 Rainfall amount data storage unit
505 Wide area ground surface moisture data storage unit
506 Server device
507 Client terminal
201 Soil moisture acquisition means
202 Ground surface moisture acquisition means
203 Estimation means
204 Soil moisture estimation means
205 First correction means
206 Second correction means
207 Slope risk degree calculation means
208 Flood risk degree calculation means
209 Risk degree presentation means

The invention claimed is:

1. A flood disaster prediction method comprising:
acquiring moisture content information in soil at a specified site;
acquiring moisture content information at a ground surface within a given range that includes the specified site;
calculating an amount of runoff or storage volume of water on the ground surface or in a ground at a freely-selected site in the given range based on the moisture content information in soil and the moisture content information at the ground;
calculating a degree of risk of flood disaster at the freely-selected site within the given range based on the amount of runoff or storage volume of water on the ground surface; and
determining and highlighting a point where there is the risk of flood disaster within the given range based on the degree of risk of flood disaster.

2. The flood disaster prediction method according to claim 1, further comprising:
estimating a parameter indicating a property of soil at the freely-selected site in the given range based on the moisture content information in soil at the specified site and the moisture content information at the ground surface within the given range, and estimates the storage volume of water on the ground surface or in a ground at the freely-selected site in the given range, based on the parameter that is estimated and an amount of rainfall at the freely-selected site.

3. The flood disaster prediction method according to claim 1, further comprising:
estimating the moisture content information in soil in each mesh element in a first area including the specified site, based on an amount of rainfall for each mesh element; and
correcting a parameter used when estimating the moisture content information in soil in each mesh element, in such a way that an estimation result of the moisture content information in soil in each mesh element in the first area comes close to the acquired moisture content information in soil at the specified site, the first area being set corresponding to at least a plurality of soil types;
estimating the storage volume of water on the ground surface or in the ground at the freely-selected site in the given range, by selecting a corrected parameter corresponding to one soil type based on the moisture content information in soil in each mesh element that is based on the amount of rainfall and is calculated using the corrected parameters corresponding to a plurality of soil types and the moisture content information at the ground surface in the given range.

4. The flood disaster prediction method according to claim 1, further comprising:
correcting a parameter used for measuring the moisture content information at the ground surface, in such a way as to come the acquired moisture content information at the ground surface in the given range including the specified site close to the acquired moisture content information in soil at the specified site, and
estimating the storage volume of water on the ground surface or in a ground at the freely-selected site in the given range, based on the moisture content information at the ground surface in the given range measured using the corrected parameter.

5. A flood disaster prediction system comprising:
at least one processing component configured to:
acquire moisture content information in soil at a specified site;
acquire moisture content information at a ground surface within a given range that includes the specified site;
calculate an amount of runoff or storage volume of water on the ground surface or in the ground at a freely-selected site in the given range based on the moisture content information in soil and the moisture content information at a ground;
calculate a degree of risk of flood disaster at the freely-selected site within the given range based on the amount of runoff or storage volume of water on the ground surface; and
determine and highlight a point where there is the risk of flood disaster within the given range, based on the degree of risk of flood disaster.

6. A non-transitory computer-readable program recording medium storing a disaster prediction program, the disaster prediction program causing a computer to execute:
processing of acquiring moisture content information in soil at a specified site;
processing of acquiring moisture content information at a ground surface within a given range that includes the specified site;
processing of calculating an amount of runoff or storage volume of water on the ground surface or in the ground at a freely-selected site in the given range based on the moisture content information in soil and the moisture content information at a ground;
processing of calculating a degree of risk of flood disaster at the freely-selected site within the given range based on the amount of runoff or storage volume of water on the ground surface; and
processing of determining and highlighting a point where there is the risk of flood disaster within the given range based on the degree of risk of flood disaster.

* * * * *